(12) United States Patent
Russin

(10) Patent No.: US 6,311,691 B1
(45) Date of Patent: Nov. 6, 2001

(54) METHOD FOR DETERMINING THE SHORTEST DISTANCE BETWEEN THE PERIPHERY OF A LESION AND THE CUT EDGE OF THE TISSUE SPECIMEN

(76) Inventor: Lincoln D. Russin, 440 Westhampton Rd., Northampton, MA (US) 01062

( * ) Notice: Subject to any disclaimer, the term of this patent is extended or adjusted under 35 U.S.C. 154(b) by 0 days.

(21) Appl. No.: 09/121,780

(22) Filed: Jul. 23, 1998

(51) Int. Cl.⁷ .................................................. A61B 19/00
(52) U.S. Cl. ...................... 128/898; 600/567; 435/40.52; 435/40.5; 604/500
(58) Field of Search ......................... 600/567; 435/40.52, 435/40.5, 4; 128/898; 604/500

(56) References Cited

U.S. PATENT DOCUMENTS

| | | | |
|---|---|---|---|
| 4,588,579 | * 5/1986 | Bachhuber et al. | 435/40.52 |
| 4,682,606 | * 7/1987 | DeCaprio | 600/567 |
| 4,911,915 | * 3/1990 | Fredenburgh | 435/40.52 |
| 4,946,669 | * 8/1990 | Seigfried et al. | 435/40.52 |
| 5,133,360 | * 7/1992 | Spears | 600/567 |
| 5,353,804 | * 10/1994 | Kornberg et al. | 600/567 |
| 5,573,008 | * 11/1996 | Robinson et al. | 600/567 |
| 5,795,308 | * 8/1998 | Russin | 600/567 |

* cited by examiner

*Primary Examiner*—David J. Isabella
*Assistant Examiner*—Kelly O'Hara

(57) ABSTRACT

A method for determining the shortest distance between the periphery of a lesion and the cut edge of the tissue specimen utilizing a cylindrical tissue specimen. The cylindrical tissue specimen is placed inside a fixative transmitting cylindrical canister for fixation. After the tissue specimen has been fixed and embedded, it is cross-section sliced in planar slices that are perpendicular to the longitudinal axis of the fixed cylindrical tissue specimen. The slicing can be performed with the tissue specimen remaining inside the cylindrical canister or the tissue specimen can be removed from the canister prior to slicing. The tissue slices are mounted on slides and the slides are evaluated to select the slide showing the lesion periphery nearest to the cut edge of the specimen. The shortest distance between the periphery of the lesion and the cut edge of the specimen is measured. Preferably, the measured distance is adjusted for artifacts in the fixation, mounting, embedding and slicing processes.

14 Claims, 5 Drawing Sheets

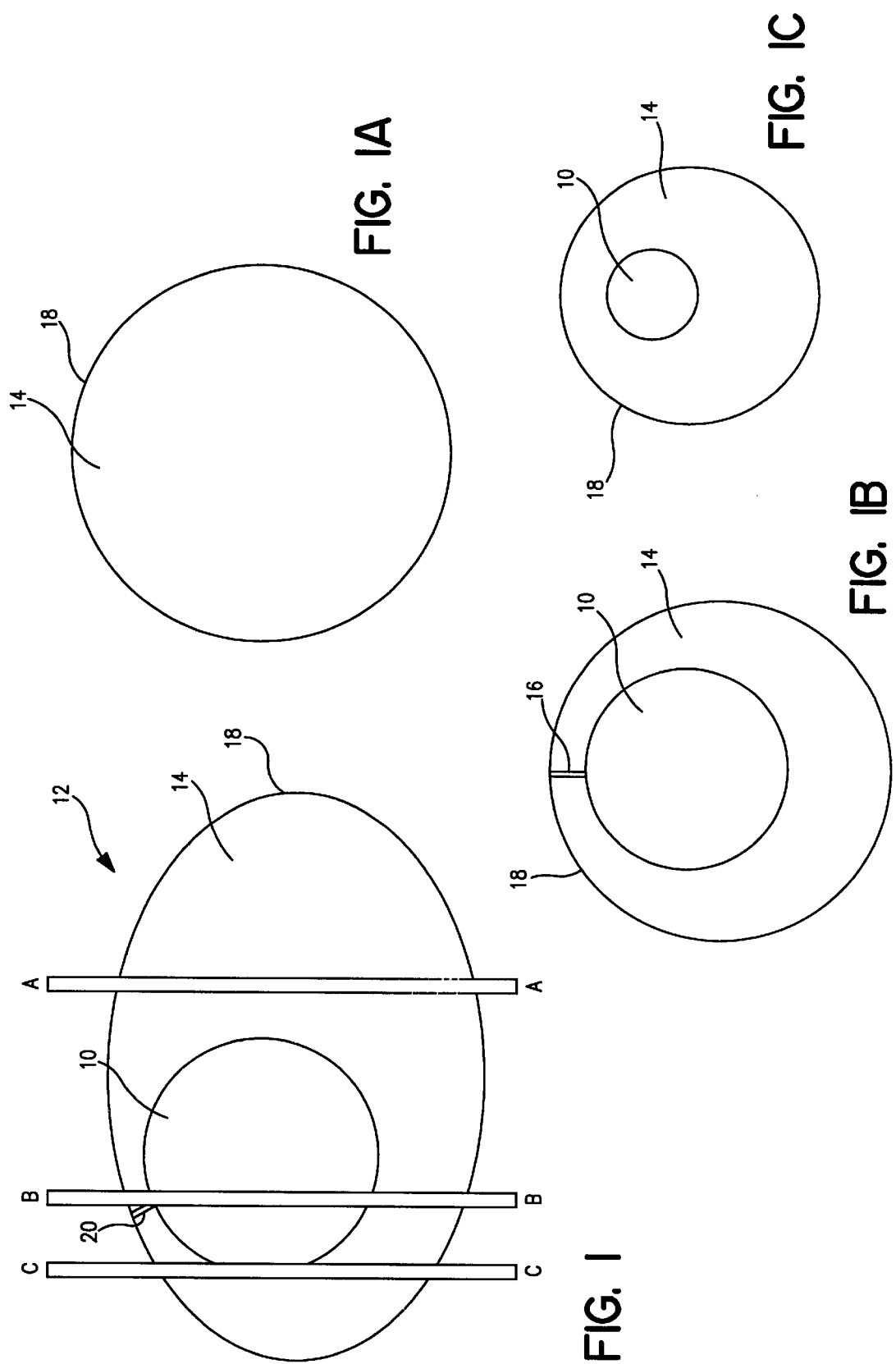

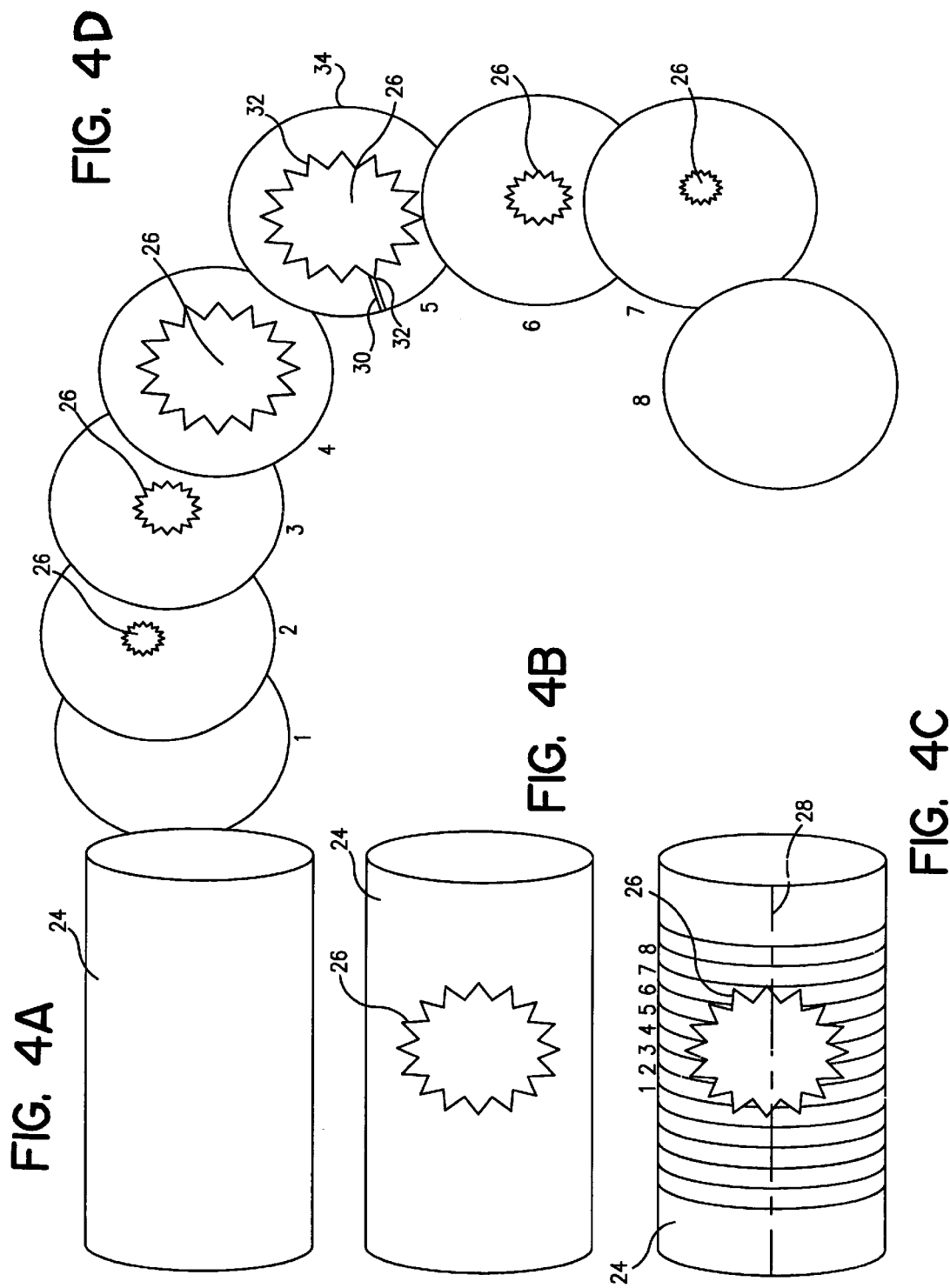

METHOD FOR DETERMINING THE SHORTEST DISTANCE BETWEEN THE PERIPHERY OF A LESION AND THE CUT EDGE OF THE TISSUE SPECIMEN

CROSS-REFERENCE TO RELATED APPLICATION

The present invention is related to applicant's application Ser. No. 08/690,185 filed Jul. 26, 1996 now U.S. Pat. No. 5,795,308 for Method and Apparati for Coaxial Breast Biopsy.

BACKGROUND OF THE INVENTION

The present invention relates to breast biopsies in general and, more particularly, to a method for accurately determining the shortest distance between the periphery of a lesion and the cut edge of a tissue specimen.

Breast biopsy evaluation methods by specimen radiography, pathologic examination of inked biopsy specimens and pathologic evaluation of additional tissue removed from the original biopsy bed in the breast (at re-excision or mastectomy) have significant limitations. No method establishes the truth of whether a lesion has been completely excised or not. Specimen radiography is a limited method of assessing completeness of excision while microscopic inspection of slices of the tissue specimen is limited by the method by which pathologists slice surgical specimens. All too often the slicing operation creates a likelihood of error in estimating the margin of excision,(i.e. the true shortest distance between the periphery of the lesion and the cut edge of the specimen). Residual tumor was found at the biopsy site in 33% of biopsies which produced specimens showing apparent complete excision. Lee and Carter, *Detecting Residual Tumor After Excision Biopsy of Impalpable Breast Carcinoma, Am. J. Roentgenology,* 1995; 164:81–86.

It is, accordingly, a general object of the invention to provide a method for accurately determining the shortest distance between the periphery of a lesion and the cut edge of the tissue specimen. If the lesion is found to be entirely within the specimen and the shortest distance from the periphery of the lesion to the cut edge of the specimen can be measured, a judgment can be made as to whether the lesion was completely excised.

BRIEF SUMMARY OF THE INVENTION

The shortest distance between the periphery of a lesion and the cut edge of a tissue specimen is determined using a cylindrical tissue specimen. The tissue specimen is placed inside a fixative transmitting cylindrical canister for fixation. Before the specimen is fixed, it can be radiographed to obtain a first estimate of whether the lesion is in the specimen and whether it appears to be completely excised. Once the specimen has been fixed and embedded, it is cross-section sliced in planar slices that are perpendicular to the longitudinal axis of the cylindrical tissue specimen. The tissue slices are mounted on slides for evaluation to select the slide showing the periphery of the lesion nearest to the cut edge of the specimen. The shortest distance between the periphery of the lesion and the cut edge of the specimen is measured. The measured distance can be adjusted for shrinkage artifacts to obtain a true shortest distance between the periphery of the lesion and the cut edge of the specimen.

BRIEF DESCRIPTION OF THE DRAWINGS

FIG. 1 diagrammatically depicts an egg with an off center yolk and three slices A—A, B—B and C—C through the egg with the shortest distance from the periphery of the yolk to the surface of the egg represented by two parallel lines;

FIG. 1A illustrates the A—A slice through the egg;

FIG. 1B illustrates the B—B slice through the egg with the apparent shortest distance represented by two parallel lines;

FIG. 1C illustrates the C—C slice through the egg;

FIG. 4A illustrates in perspective a cylindrical tissue specimen;

FIG. 4B depicts the tissue specimen as though it were transparent and shows a lesion in the tissue;

FIG. 4C is similar to FIG. 4B and illustrates a series of planar slices of the cylindrical tissue specimen that are taken perpendicular to the longitudinal axis of the cylindrical tissue specimen with the slices numbered 1 through 8;

FIG. 4D illustrates in sequence the slices 1–8 of FIG. 4C with slice 5 showing the true shortest distance from the periphery of the lesion to the cut edge of the tissue specimen; and, FIG. 5 is a flow diagram in block form illustrating the steps of the method for determining the shortest distance from the periphery of a lesion to the cut edge of the tissue specimen.

DETAILED DESCRIPTION OF A PREFERRED EMBODIMENT

Figure 2B:
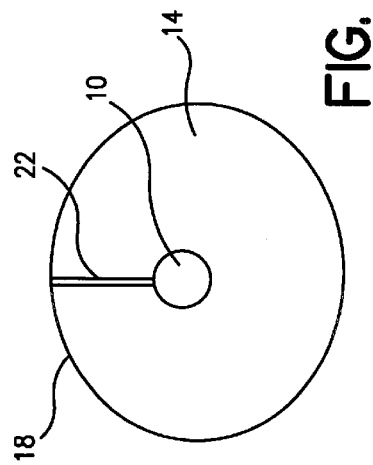
FIG. 2B illustrates the B—B slice through the egg with the apparent shortest distance represented by two parallel lines.
Figure 2C:
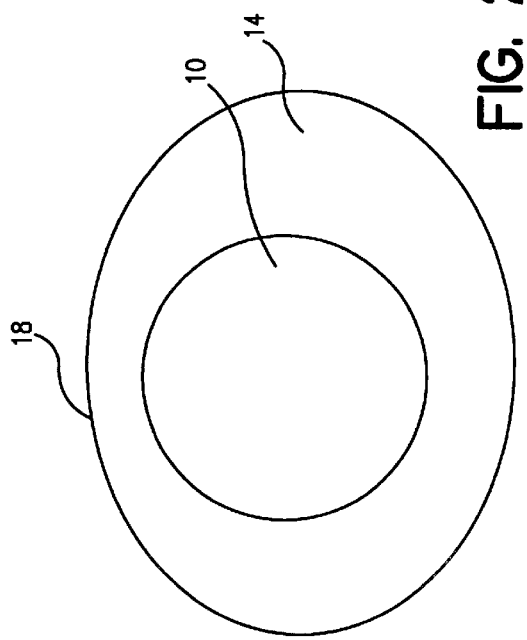
FIG. 2C illustrates the C—C slice through the egg.
Figure 2:
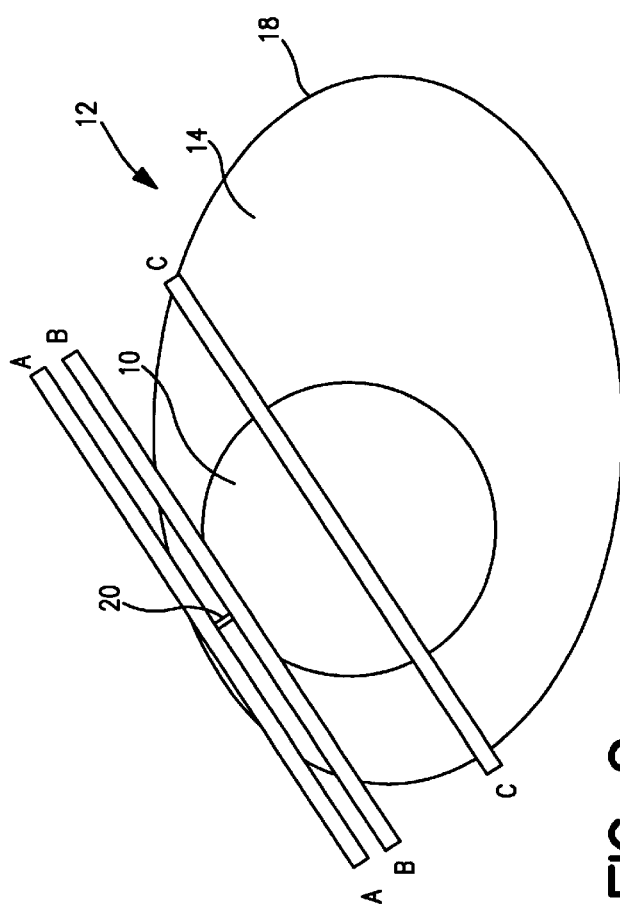
FIG. 2 is similar to FIG. 1 with the slices A—A, B—B and C—C slanted with respect to the long axis of the egg and again the shortest distance from the periphery of the egg yolk to the surface of the egg is represented by two parallel lines.
Figure 2A:
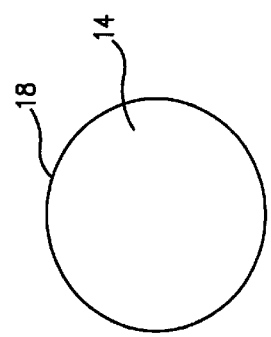
FIG. 2A illustrates the A—A slice through the egg.
Figure 3A:
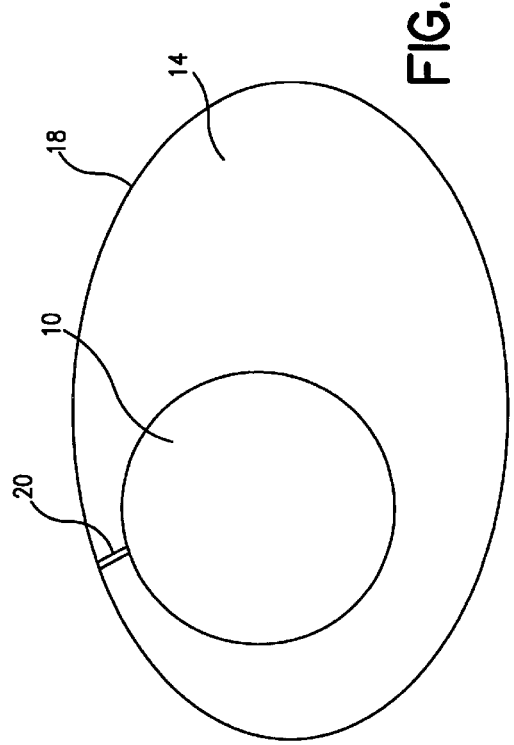
FIG. 3A depicts the egg as though it were transparent with the shortest distance again represented by two parallel lines.
Figure 3C:
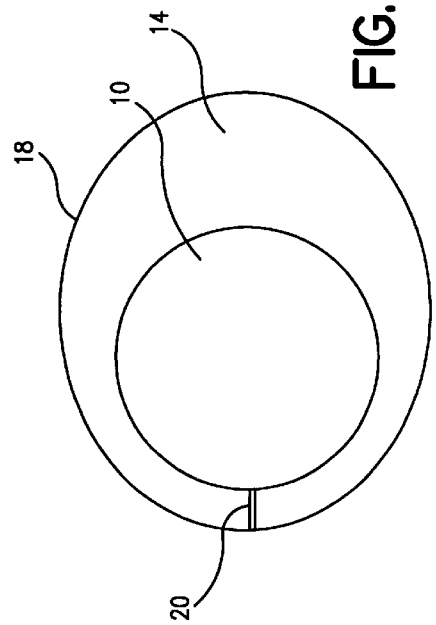
FIG. 3C shows the D—D slice with the shortest distance again represented by two parallel lines that are the same length as those shown in FIG. 3A which is the shortest distance.
Figure 3:
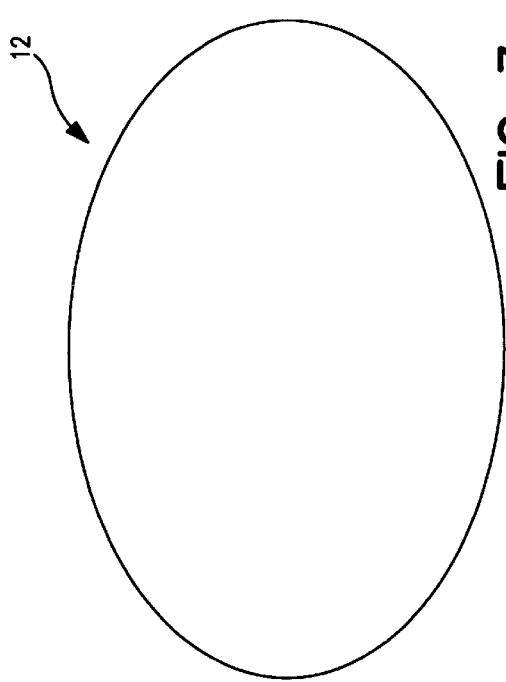
FIG. 3 depicts an egg.
Figure 3B:
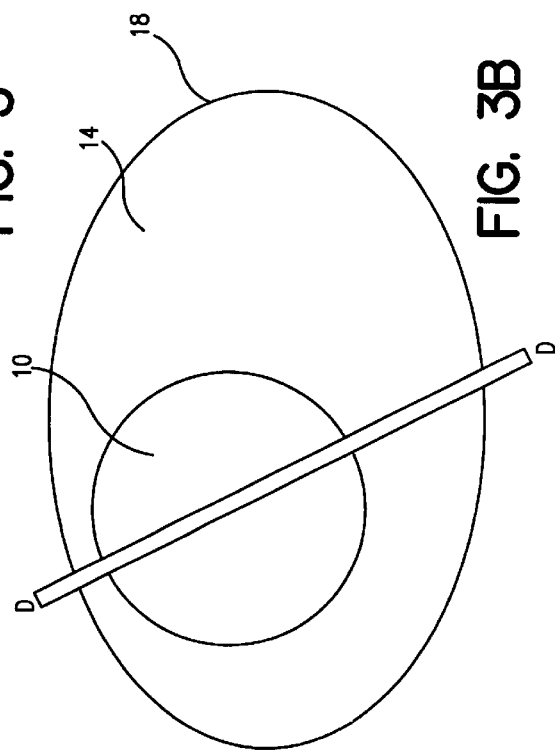
FIG. 3B shows slice D—D taken parallel to the shortest distance depicted in FIG. 3A.

Turning now to the drawings, FIGS. 1 through 3 illustrate the problem of determining the shortest distance from the periphery of a lesion to the cut edge of the specimen using an egg/yolk analogy.

Normally pathologists place the biopsy specimen on a cutting board and make several parallel slices with a scalpel, like one might slice an egg, to reveal the lesion within the specimen and demonstrate the minimum distance between the periphery of the lesion and the cut edge of the specimen (margin of resection). Usually the lesion is not visible on inspection of the unsliced specimen, but it might be felt as a firm area, or visible on a specimen x-ray. Consider the lesion as a yolk 10 within a hard-boiled egg 12. The yolk, like the lesion in the specimen, is not visible within the egg. If an egg is sliced in the way most pathologists slice biopsy specimens, i.e., slice A—A, B—B and C—C, slices immediately adjacent to the yolk would show no yolk (FIG. 1A), while others (FIGS. 1B and 1C) through the yolk would show a cross-section of yolk surrounded by varying thicknesses of egg white 14. A measurement of the apparent shortest distance 16 (FIG. 1B) from the yolk to the surface 18 of the egg could over-estimate the true distance 20 (FIG. 1) because the slices would not necessarily be oriented parallel to the true shortest distance between the yolk and the surface of the egg. Slices would most likely be at an angle (FIGS. 2 and FIGS. 2A–2C), which would result in a longer apparent distance 22 (FIG. 2B) and an over-estimation of the true shortest distance 20 (FIG. 1). For evaluation of breast biopsy specimens, the pathologist would likely over-estimate the true margin of resection because the slices through the specimen would probably not parallel the true shortest distance between the lesion and the cut edge of the specimen. This would result in an overconfidence that the specimen was excised with an adequate margin of resection, and possibly give a mistaken impression that the specimen had been completely excised. An infinite number of slices would be needed with three-dimensional reconstruction of the position of the yolk within the egg (or the lesion within the specimen) to allow an accurate measurement of the shortest distance between the yolk and the surface of the egg (or the margin of resection of the lesion in the biopsy specimen).

Continuing the egg analogy, if the slice D—D is taken parallel to the true shortest distance 20, (FIGS. 3A and 3C), this distance can be accurately determined. However, this would require prior knowledge of the position of the yolk in the egg.

Referring now to FIGS. 4A through 4C, these Figures diagrammatically illustrate the concept of the method of the present invention. FIG. 4A depicts a cylindrical tissue specimen 24 containing a lesion 26 (FIGS. 4B and 4C shown with transparency). The lesion containing specimen is cross-sectioned sliced in a plurality of planar slices that are perpendicular to the longitudinal axis 28 of the cylindrical tissue specimen.

FIG. 4D illustrates sequentially from top to bottom the results of slicing from left to right the FIG. 4C tissue specimen. The slices 1 through 8 in FIG. 4C are correspondingly numbered in FIG. 4D. The slice identified as number 5 shows the shortest distance 30 from the periphery 32 of the lesion 26 to the cut edge 34 of the tissue specimen.

Figure 5:
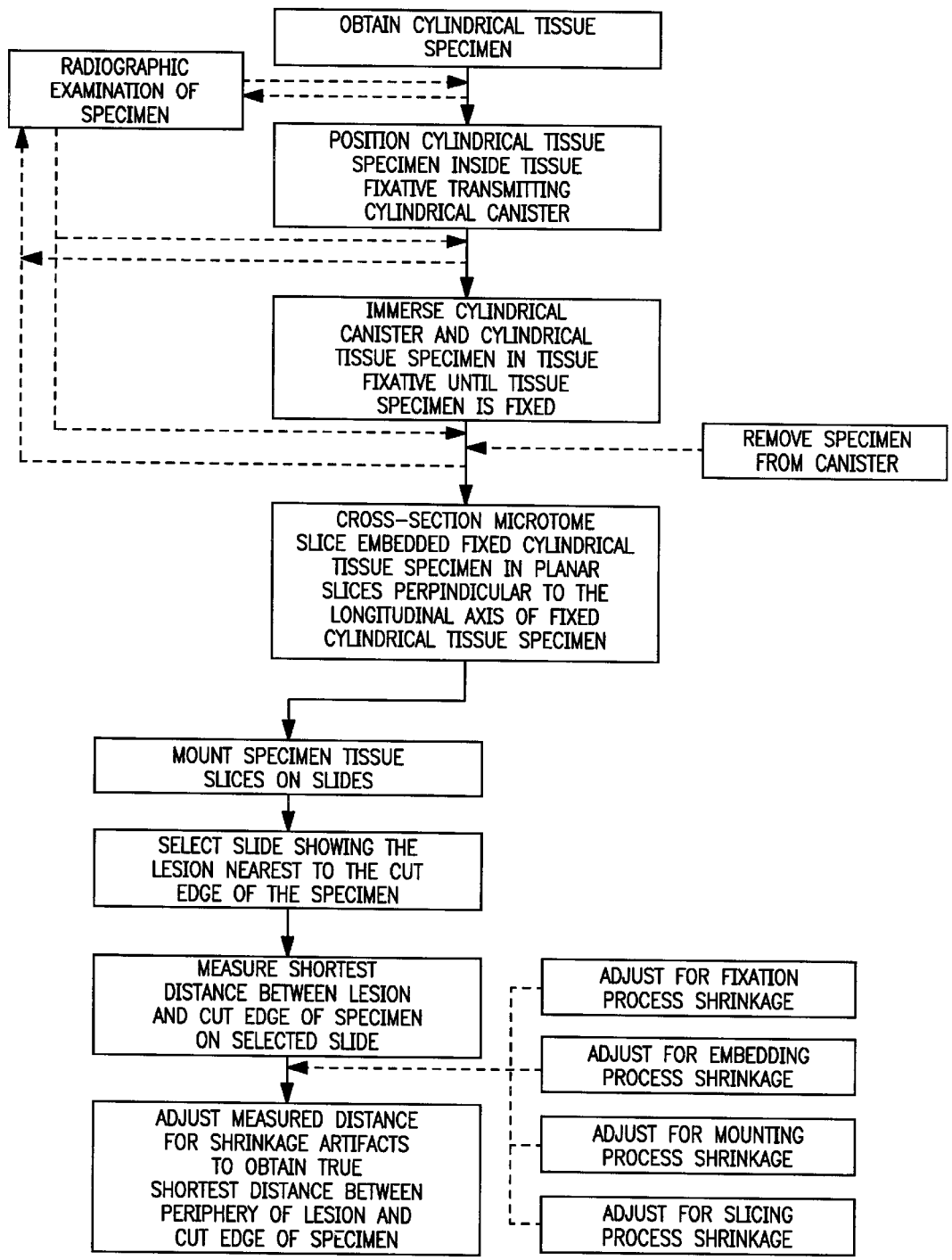

The concept illustrated in FIGS. 4A through 4D is depicted in the flow diagram of FIG. 5 showing the steps of the method of the present invention.

A cylindrical tissue specimen is obtained from the patient. One method for obtaining such a cylindrical tissue specimen is disclosed in my co-pending application Ser. No. 08/690,185 filed Jul. 26, 1996 for Method and Apparati for Coaxial Breast Biopsy which is incorporated herein by reference (see in particular FIGS. 20–23, 25A–25C and associated text).

After obtaining the cylindrical tissue specimen, it is placed in a cylindrical canister. The canister transmits a standard tissue fixative e.g., 10% formalin to the tissue specimen. Transmission of the fixative can be through apertures in the cylindrical canister or through the canister material itself e.g. cellulose or plastic. It should be understood that the specimen can be radiographed before or after being placed in the canisters since the canister is not opaque to x-rays.

The tissue specimen containing canister is immersed in a tissue fixative until the specimen is fixed. At this point in the process, the specimen can be removed from the canister if desired. Alternatively, the specimen can be kept in the cylindrical canister. In either case, the fixed cylindrical tissue specimen is embedded in an embedding material such as paraffin.

After embedding, the fixed cylindrical tissue specimen is cross-section microtome sliced in planar slices that are perpendicular to the longitudinal axis of the fixed cylindrical tissue specimen to produce slide mountable tissue specimen slides. The true shortest distance within generally accepted medical practice will lie in a plane perpendicular to the longitudinal axis of the fixed cylindrical tissue specimen. It should be understood that the tissue specimen can be sliced into parallel "thick" slices and then embedded for subsequent microtome slicing with sampling every "n" slices or microtome sliced directly after embedding with sampling every "n' slices.

The specimen tissue slices are mounted on slides for evaluation to determine the presence of any lesion in the specimen tissue slices. If a lesion is present, the slide showing the periphery of the lesion nearest to the cut edge of the specimen is selected. The shortest distance between the periphery of the lesion and the cut edge of the specimen is then measured. This measured distance or "margin of resection", colloquially known as a "surgical margin" can then be used to judge the "completeness of excision".

It is known that the processes of fixation, embedding, mounting and slicing can produce dimensional changes in the tissue specimen. Preferably, the measured distance is adjusted for shrinkage artifacts to obtain a true shortest distance between the lesion periphery and the cut edge of the specimen.

The FDA requires radiographic examination of the specimen as well as histologic verification that the lesion appears to have been completely excised. The radiographic examination can be performed at a variety of points in the process as depicted in FIG. 5 by the dotted lines.

Having described the method of the invention, it will now be apparent to those skilled in the art that numerous modifications can be made therein without departing from the scope of the following claims.

What I claim is:

1. A method for processing tissue specimens comprising the steps of:
    (a) obtaining a cylindrical tissue specimen having a longitudinal axis and an outside diameter;
    (b) positioning the cylindrical tissue specimen inside a cylindrical canister having an inside diameter slightly larger than the outside diameter of the cylindrical tissue specimen, said cylindrical canister permitting transmission of a tissue fixative to the cylindrical tissue specimen to allow fixation thereof;
    (c) immersing the cylindrical canister with the cylindrical tissue specimen positioned therein in a tissue fixative until the cylindrical tissue specimen is fixed;
    (d) embedding the fixed cylindrical tissue specimen;
    (e) cross-section microtome slicing the embedded, fixed cylindrical tissue specimen in a plurality of planar slices that are perpendicular to the longitudinal axis of the fixed cylindrical tissue specimen;
    (f) mounting the specimen tissue slices on slides;
    (g) evaluating the slides to determine the presence of any lesion in the specimen tissue slices and, if present, selecting the slide showing the periphery of the lesion nearest to the cut edge of the specimen; and,
    (h) measuring the shortest distance between the periphery of the lesion and the cut edge of the specimen on said selected slide.

2. The method of claim 1 further comprising the step of removing the fixed cylindrical tissue specimen before performing Steps (d) through (h).

3. The method of claim 1 wherein said fixed cylindrical tissue specimen is cross-section sliced while positioned inside the cylindrical canister so that both the tissue specimen and the canister are so sliced.

4. The method of claim 1 wherein the evaluation of the slides is performed by optical examination.

5. The method of claim 1 further comprising the step of performing a radiographic examination of said cylindrical tissue specimen or said fixed cylindrical tissue specimen prior to step (e).

6. A method for processing tissue specimens comprising the steps of:

(a) obtaining a cylindrical tissue specimen having a longitudinal axis and an outside diameter;

(b) positioning the cylindrical tissue specimen inside a cylindrical canister having an inside diameter slightly larger than the outside diameter of the cylindrical tissue specimen, said cylindrical canister permitting transmission of a tissue fixative to the cylindrical tissue specimen to allow fixation thereof;

(c) immersing the cylindrical canister with the cylindrical tissue specimen positioned therein in a tissue fixative until the cylindrical tissue specimen is fixed;

(d) embedding the fixed cylindrical tissue specimen;

(e) cross-section microtome slicing the embedded, fixed cylindrical tissue specimen in a plurality of planar slices that are perpendicular to the longitudinal axis of the fixed cylindrical tissue specimen;

(f) mounting the specimen tissue slices on slides;

(g) evaluating the slides to determine the presence of any lesion in the specimen tissue slices and, if present, selecting the slide showing the periphery of the lesion nearest to the cut edge of the specimen;

(h) measuring the shortest distance between the periphery of the lesion and the cut edge of the specimen on said selected slide; and, (i) adjusting said measured distance for shrinkage artifacts in order to obtain a true shortest distance between the periphery of the lesion and the cut edge of the specimen.

7. The method of claim 6 further comprising the step of adjusting said measured distance for shrinkage artifacts in the mounting process.

8. The method of claim 6 further comprising the step of adjusting said measured distance for shrinkage artifacts in the slicing process.

9. The method of claim 6 further comprising the step of adjusting said measured distance for shrinkage artifacts in the fixation process.

10. The method of claim 6 further comprising the step of adjusting said measured distance for shrinkage artifacts in the embedding process.

11. The method of claim 6 further comprising the step of removing the fixed cylindrical tissue specimen before performing steps (d) through (i).

12. The method of claim 6 wherein said fixed cylindrical tissue specimen is cross-section sliced while positioned inside the cylindrical canister so that both the tissue specimen and the canister are so sliced.

13. The method of claim 6 wherein the evaluation of the slides is performed by optical examination.

14. The method of claim 6 further comprising the step of performing a radiographic examination of said cylindrical tissue specimen or said fixed cylindrical tissue specimen prior to step (e).

* * * * *